United States Patent [19]

Diamond

[11] Patent Number: 4,474,185
[45] Date of Patent: Oct. 2, 1984

[54] BODY MOVEMENT DETECTOR

[76] Inventor: Donald A. Diamond, 5416 Harbor Rd., Bradenton, Fla. 33529

[21] Appl. No.: 377,703

[22] Filed: May 12, 1982

[51] Int. Cl.$^3$ .............................................. A61B 5/10
[52] U.S. Cl. .................................................. 128/722
[58] Field of Search ................ 128/721, 722; 340/562, 340/573

[56] References Cited

U.S. PATENT DOCUMENTS 3,973,208 8/1976 Diamond ............................ 340/562
3,991,746 11/1976 Hanna ................................. 340/573
4,381,788 5/1983 Douglas ............................. 128/722

Primary Examiner—Kyle L. Howell
Assistant Examiner—Deidre A. Foley
Attorney, Agent, or Firm—Duckworth, Allen, Dyer & Pettis

[57] ABSTRACT

A capacitance type motion detector adapted to monitor an infant or a person in bed to provide an alarm for apnea episodes. A conductive grid array is provided on a plastic film or the like and disposed adjacent the person to be monitored. A 50 kHz oscillator having a floating circuit ground and an output connected to an earth ground pumps the earth ground. A voltage follower preamplifier having a common circuit ground with the oscillator is connected to the grid array which picks up the 50 kHz signal. Motion, such as breathing, of the person being monitored varies the capacitance to earth ground of the grid array thereby modulating the 50 kHz signal. The modulation envelope is detected, amplified and applied to a comparator. An alarm circuit produces a first output indication for each detected motion and a second output for absence of motion for a selectable time period. The second output in an apnea monitor may produce an alarm to permit immediate attention to the person.

7 Claims, 4 Drawing Figures

BODY MOVEMENT DETECTOR

BACKGROUND OF THE INVENTION

1. Field of the Invention

The present invention relates generally to a device for monitoring vital body movements and more particularly to a device for detecting episodes of apnea in infants.

2. Description of the Prior Art

In recent years, progress has been made in diagnosing the so-called "crib death" problem in which infants have died during sleep. It has been found that a significant percentage of infants up to the age of about one year may have problems in the involuntary breathing system such that, during sleep, respiration may cause, a condition often referred to as apnea. In most instances, the infant will begin breathing again spontaneously. However, if the duration of an apnea episode is excessive, irreversible cerebral damage may be sustained, and in some cases death occurs. Methods have been devised to determine which infants may have this problem.

When this condition is determined for an infant, it is necessary that the parents have a means for detecting the onset of an episode so that the infant may be assisted in restarting breathing. Although a number of efficient devices have been developed for use in hospitals for premature infants as well as other patients to monitor and produce an alarm when normal breathing stops, the cost and complexity of such devices precludes the average family from their use. Some units have been developed which are better adapted to home use but still suffer from problems of high cost and often from tendency to false alarms. Therefore, there is a need for a highly reliable and low cost unit that will be within the reach of even low income families.

Various types of apnea monitoring devices are described in the following patent Nos.:

3,875,929 Grant;
3,926,177 Hardway et al.;
3,727,606 Sielaff;
3,942,513 Frank;
3,903,876 Harris.

Grant teaches a microwave scanner which provides a movement sensitive field. However, the expense of providing what amounts to a radar transmitter and receiver contributes to an undesired high cost. In the patent to Hardway et al., a capacity pad or mattress is used in which the body lying on it will cause capacity variations with movement. A complex capacitance measuring circuit is required and a capacitive rate change measuring circuit is used. Sielaff teaches a fluid type mattress connected to a pressure transducer for measuring the variations in pressure with breathing and other movements. An extremely sensitive transducer must be used since the breathing of an infant would produce very minute variations in pressure. In the Frank patent, a closed loop monitor and stimulator is taught which uses a sensor attached to the patient and a stimulator which is energized when lack of breathing is sensed. The stimulator must be maintained in proper contact with the infant and requires a pneumatic supply unit for its operation. Harris discloses a monitor which is primarily used with a tracheostomy tube.

None of the known prior art apnea monitoring devices appear practical for low cost production for home use.

SUMMARY OF THE INVENTION

The present invention is a capacitance type motion monitor in which very small variations in capacity of a capacitance array are measured and used with appropriate timing circuits to provide an alarm when cessation of motion is noted for a predetermined period. Advantageously, I utilize a capacitance monitoring procedure disclosed in my U.S. Pat. No. 3,973,208 entitled "Capacitor Detector Device", and incorporate the specification of that patent by reference.

Although many types of capacitance arrays are suitable for use in my invention, I prefer to utilize a pad which may be used over a crib mattress or the like, and upon which the infant or patient may lie. In its basic form, the pad includes a plastic film having a zig-zag like grid pattern formed over the area thereof from a thin metallic foil or the like. A second plastic film may have a solid foil covering and may be bonded to the array film in a sandwich fashion such that the solid sheet acts as a guard shield for the grid array to minimize external interference. The array or grid pattern may be overlaid with a third plastic sheet and bonded thereto for protection.

The above described capacitance pad includes leads from the foil grid and from the guard shield foil. In use, the pad may be attached to the mattress or may be used as part of an acrylic or polyester filled mattress-like pad. In this form, the infant or patient to be monitored would sleep over the gridded portion of the pad. Alternatively, the capacitance pad may be mounted either horizontally or vertically over or adjacent to a crib or bed if desired. The electrical lead from the grid pattern is connected to the input of a voltage follower preamplifier with the guard shield foil connected to the voltage follower output. Thus, the guard shield foil is at essentially the same potential as the grid. An oscillator which may produce a square wave output waveform at 50 kHz is provided having a common electrical ground with the preamplifier although other frequencies are also suitable. The output of the oscillator, however, is connected to an earth ground. For example, when used in a home, the grounded third wire of the normal household electrical outlet may be used for this ground. As explained in detail in my U.S. Pat. No. 3,973,208 referenced above, the oscillator pumps the earth ground with respect to the internal or floating ground of the preamplifier and in this instance, the grid array.

The result of pumping the earth ground is a 50 kHz carrier frequency voltage appearing between the grid array and the preamplifier ground. As may now be understood, any objects between the capacitance pad array grid and the earth ground, which in this case is represented by the wiring in the room as well as various metal objects, will act as a dielectric and will change the amplitude of the 50 kHz carrier signal applied to the preamplifier.

It will be apparent that the grid array may be used without the guard shield in which instance, the system will be sensitive to movements on either side of the array. Advantageously, when used in an apnea monitor, the guard shield limits the response to movements facing the array.

When used as the apnea alarm of the present invention, the capacitance of the array with respect to earth ground will continuously vary with movement of the infant as occasioned by normal breathing. When the infant is asleep, cessation of breathing will result in a period of no capacitive change and therefore a steady signal into the preamp. When the infant is breathing normally, the output of the preamp will be a time varying amplitude 50 kHz signal due to the time variation in dielectric constant. It is desirable to utilize a 60 Hz notch filter ahead of the voltage follower to eliminate possible power line signal interference and, in some cases, a narrow band 50 kHz band pass filter to minimize other signals which might be picked up by the sensitive voltage follower. The time varying 50 kHz signal from the voltage follower is rectified to produce a low frequency time varying envelope. This signal is capacitively coupled to a high gain, low frequency amplifier which amplifies further the slowly varying signal from the rectifier. The output of this amplifier is coupled to one input of a comparator which is set to produce a HIGH output when there is no change in the signal from the low frequency amplifier. Thus, a LOW will appear when the signal from the rectifier increases due to a change in capacity of the capacitance pad. An event indicator connected to the output of the comparator is arranged to illuminate an LED or the like when the output of the comparator swings LOW; thus, the event indicator light will normally flash periodically as the infant breathes normally. A cessation of breathing would be indicated by the event indicator being dark. The output from the comparator drives an RC integrating circuit in which the capacitor is slowly charged while the output is HIGH and is rapidly discharged when the output is LOW. The voltage across the capacitor provides an input to an alarm comparator in which the comparator threshold is adjusted to trigger the comparator after about three time constants of the RC circuit.

As may be understood, the time constant of the RC circuit is selected with respect to the normal breathing rate such that the three time constant delay period would be indicative of interruption of breathing but short enough so that an alarm can be sounded and attention provided to the infant before enough time for physiological damage to occur. Thus, when a potentially dangerous episode of apnea occurs, the alarm comparator will be triggered and the HIGH output used to enable an SCR circuit having a dc power supply. Once fired, the SCR will remain conducting until reset. The SCR may be utilized to sound an audible alarm and also to illuminate a visual alarm to indicate the potentially dangerous episode.

Through the use of the technique of pumping the earth ground from an oscillator, a signal well above the noise level will be generated at the voltage follower input by even the small breathing movements of an infant near the capacitive pad such that a relatively simple amplifier and associated logic circuits can detect dangerous apnea episodes and initiate an alarm. By the use of operational amplifiers and comparators, the majority of the electronic circuits may be fabricated as integrated circuits at a fraction of the cost of the more complex prior art apnea monitoring circuits. The percentage of the newborn babies that may be prone to the apnea problem is estimated to be extremely large. Therefore, the development of a single LSI type chip for the major portion of the monitor is entirely practical and may well reduce the cost of a unit such that every family with an infant having this problem can be provided with a monitor. Similarly, concerned parents of infants in which the tendency has not been diagnosed may wish to use a monitor during the early months as an exercise of caution.

Although the invention is eminently suitable for use in an apnea alarm, it has many other applications as a sensitive proximity switch such as an intruder alarm, a machine safety switch, counters and the like.

It is therefore a principal object of the invention to provide an apnea monitor to energize an alarm after an infant or patient has stopped breathing for a selected time period.

It is another object of the invention to provide an apnea monitor that can be fabricated and sold at a low cost to permit families with newborn infants to be able to monitor the infants breathing during sleep.

It is still another object of the invention to provide a device suitable for use in hospitals, nursing homes, and the like that can be made available at low cost for monitoring movements of patients in bed and for monitoring when a patient quits breathing or leaves the bed.

It is yet another object of the invention to provide an apnea monitoring device having a capacitance pad and an electronic circuit which senses small changes in capacitance of the capacitance pad due to changes in dielectric constant thereof.

It is a further object of the invention to provide an electronic circuit for use with an apnea monitor which can be implemented by large scale integration.

It is still a further object of the invention to provide a capacitance measuring system having a capacitance pad in which the earth ground is pumped by an oscillator and a change in capacitance is indicated by a change in the envelope of the oscillator waveform in the monitoring circuit.

It is another object of the invention to provide a capacitance pad having a floating grid array connected to the input of a single ended voltage follower and a guard shield connected to the output of the voltage follower to thereby shield the pad from objects opposite the guard shield.

It is another object of the invention to provide an apnea monitor which includes an indicator that will flash at the breathing rate of the person being monitored, and which will energize a visual and an audible alarm when normal breathing ceases.

It is another object of the invention to provide a sensitive proximity switch having a shielded floating input capacitance element in which the earth ground is pumped.

These and other objects and advantages of the invention will become apparent from the following detailed description and the drawing.

DETAILED DESCRIPTION OF THE PREFERRED EMBODIMENT

Figure 1:
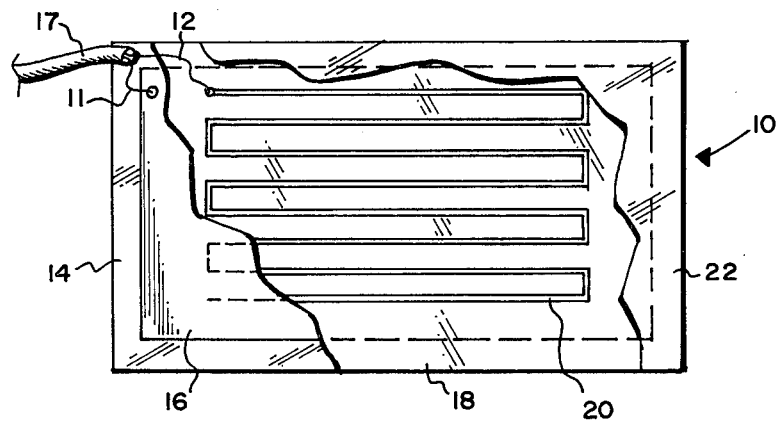
FIG. 1 is a partially cut away capacitance pad in accordance with my invention.

The apnea monitoring device of the invention is applicable to many uses for which slight movements of a person are to be detected. However, the invention will be explained for use as an apnea monitor and in particular for monitoring the breathing of infants during sleep. As shown in the cutaway view of FIG. 1, the capacitive pad 10 is illustrated in cutaway view. This implementation is suitable for use in a crib or bed. Although many alternative constructions will be apparent, I prefer here to utilize a lower plastic sheet 14 which may be two or more mils thick. A conducting sheet of foil 16 or the like is cemented or otherwise attached to lower sheet 14 and, as will be described, serves as a guard shield for the capacity grid array. An electrical connection 11 is made to foil 16. A middle sheet of plastic film 18 covers lower sheet 14 and foil 16. Next, a grid array 20 as the capacitance element is cemented to middle sheet 18. Although I show an array formed by parallel strips of foil joined at alternate ends, it will be understood that a zig-zag pattern, a helical pattern, or other similar patterns would be entirely suitable. An electrical lead 12 connects to array foil 20. A top sheet of plastic film 22 is laid over the middle sheet 18 and the edges of the three plastic sheets 14, 18, and 22 are cemented or thermally bonded together. Thus, the plastic sheets serve to protect the foils and to act as insulation and dielectric material with respect to the capacitive pad 10.

Figure 2:
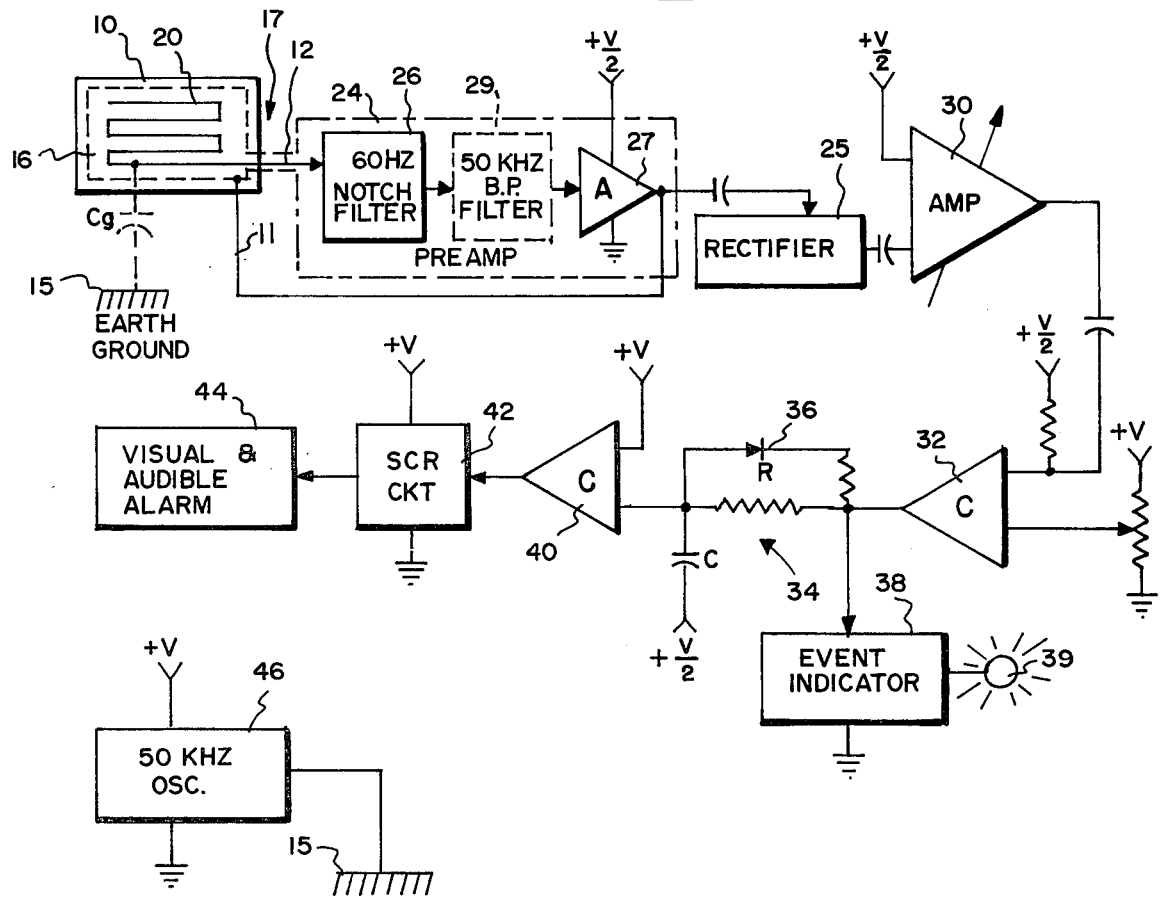
FIG. 2 is a simplified block diagram of the capacitance pad of FIG. 1 and the electronic circuits for detecting variations in the capacitance of the pad.

Capacitive pad 10 may be made into a quilt cover or a mattress pad to be used over an existing mattress, or may be mounted integral with the mattress. In a typical use of the capacitance pad 10, it is placed on the top surface of a crib mattress and a conventional sheet or mattress cover installed over the pad 10. Leads 11 and 12 are preferably connected to a shielded cable 17 for connection to the electronic detector portion of the invention. Turning now to FIG. 2, a simplified block diagram of the electronic detection portion of my apnea monitor is shown. Capacitance pad 10 is shown with the guard shield foil 16 represented by the dashed lines and the grid array pattern 20 indicated by the solid lines. As may be understood, a certain capacitance $C_s$ will exist between the shield foil 16 and the earth ground 15 as indicated by the dashed symbol. This capacitance will be a function of the position of capacitance pad 10 with respect to various conducting earth grounds in the vicinity and of the dielectric constant of any material between the elements and such earth grounds.

Output lead 12 in cable 17 from grid array 20 connects to voltage follower preamp 24 while the lead 11 to shield foil 16 and the shield of cable 17 connects to the voltage follower 27 output of the electronic portion of the invention. Preamp 24 consists of an operational amplifier 27 connected as a voltage follower and a 60 Hz notch filter between grid array 12 input and voltage follower 27. An optional filter 29 has a narrow bandpass centered at about 50 kHz. A 50 kHz oscillator 46 has its output connected to an earth ground point. The output of oscillator 46 will "pump" earth ground 15 with respect to the electronic system ground. Thus, an ac voltage at 50 kHz will appear across capacitance $C_g$. When no change is occurring in the capacitance $C_g$, a steady 50 kHz signal will occur on lead 12 and will drive voltage follower preamp 24. The 60 Hz notch filter 26 serves to prevent small signals picked up by capacitance pad 10 from the 60 Hz power line from reaching amplifier 27 and reducing its sensitivity to the desired 50 kHz signals. Bandpass filter 29 may be used in environments having other interfering signals such as may be present in hospitals which utilize various radio frequency and interference generating electronic devices.

As will be understood, the voltage at the output of voltage follower 27 will be essentially equal to the voltage between lead 12 and circuit ground. Since guard shield 16 is connected to the output of voltage follower 27 by lead 11, there is essentially no potential therebetween and guard shield 16 serves effectively to prevent any objects on the backside of pad 10 from affecting the net capacitance thereof.

The output from voltage follower 27 is fed to rectifier 25 which will produce a dc voltage proportional to the amplitude of that signal. Amplifier 30 is a low frequency amplifier and is capacitively coupled to rectifier 25 to eliminate the dc component of the rectified output of preamp 24.

Figure 3:
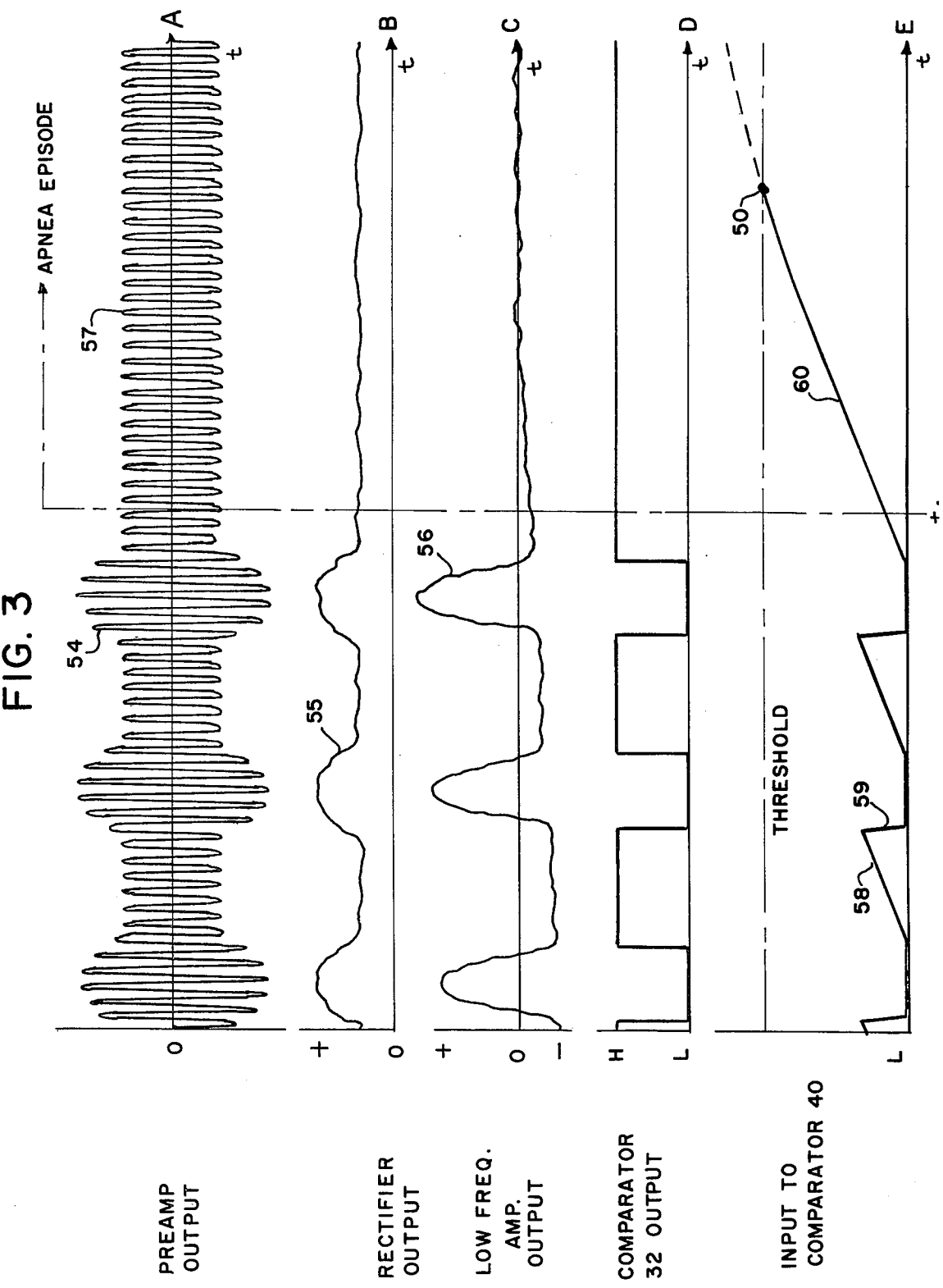
FIG. 3 is a set of waveform diagrams occuring at various points in the circuit of FIG. 2.

As may now be seen, when there are no changes occurring in the capacitance pad, there will be essentially no output from amplifier 30. Assume now that an infant is sleeping on capacitance pad 10. As the infant breathes, the slight motions of its body will result in a change of dielectric constant of capacitance $C_g$ with a resultant capacitance change. Therefore, the 50 kHz voltage across that capacitance and therefore the voltage appearing on lead 12 will also change. A typical voltage for this condition at the output of voltage follower 27 is shown in the graph of FIG. 3 on line A. Here, the regular breathing movements of the infant result in an amplitude modulation 54 of the 50 kHz signal producing the noted increase of amplitude. The rectifier output will also change and will essentially reproduce the envelope 55 of the preamp output as shown on line B. During periods of regular breathing, the ac coupling from rectifier 25 to amplifier 30 will result in the waveform 56 shown on line C which will have a zero dc average voltage. If the infant should stop breathing at time $t_1$, which would represent the beginning of an apnea episode, the physical movement stops and the preamp output on line A will be the steady 50 kHz signal 57. At this point, the rectifier output on line B will be essentially steady, modulated only by system noise. The output from amplifier 30 will then approach zero. Amplifier 30 may have a high frequency cutoff of a few Hertz to minimize effects of noise on the system.

Amplifier 30 is coupled to comparator 32 which has an adjustable threshold. This threshold is adjusted with no signal from capacitance pad 10 to produce a HIGH at the output of comparator 32 as indicated on line B. During normal breathing, the output of amplifier 30 will drive the input to comparator 32 below the threshold level causing the output to go LOW. Thus, a negative going pulse will be produced for each signal produced by breathing movement. The output of comparator 32 drives RC circuit 34. When the output of comparator 32 goes HIGH, it will charge capacitor C through resistor R as indicated on line E at 58. The time constant of the RC circuit is selected such that during a normal respiration cycle, C will charge to only a fraction of the charging voltage. When the output of comparator 32 goes LOW, the charge on capacitor C will be discharged through diode 36 as indicated at 59. The discharge path is through event indicator 38 which responds to the LOW output from comparator 32 to energize LED 39. Thus, during each discharge, LED 39 will flash. This permits an observer to monitor remotely that the infant is breathing normally.

At the beginning of an apnea episode at $t_1$, breathing ceases, the low frequency amplifier output remains essentially zero and the output of comparator 32 remains HIGH. Therefore, capacitor C will tend to charge to the HIGH value shown at 60 on line E of FIG. 3. The voltage across capacitor C is monitored by alarm comparator 40 which has a preset threshold. This threshold is selected to be equal to that voltage on capacitor C which is reached after several time constants. Thus, when the voltage 60 across C increases as indicated on line E during an apnea episode to point 50, which represents the threshold for comparator 40, the output of comparator 40 goes HIGH and triggers silicon control rectifier (SCR) circuit 42. The SCR circuit energizes a visual and audible alarm 44 to alert an observer to the apnea episode.

The values of RC circuit 34 are selected such that the alarm occurs early enough to permit a person monitoring to reach the infant and to assist it in restarting of breathing before physiological damage can occur. For example, a 15–20 second period is typical. SCR circuit 42 operates from a dc voltage supply V and therefore must be manually reset to turn off the alarm 44. An early warning of the onset of an apnea episode is also indicated by cessation of the flashing of the LED of event indicator 38.

Figure 4:
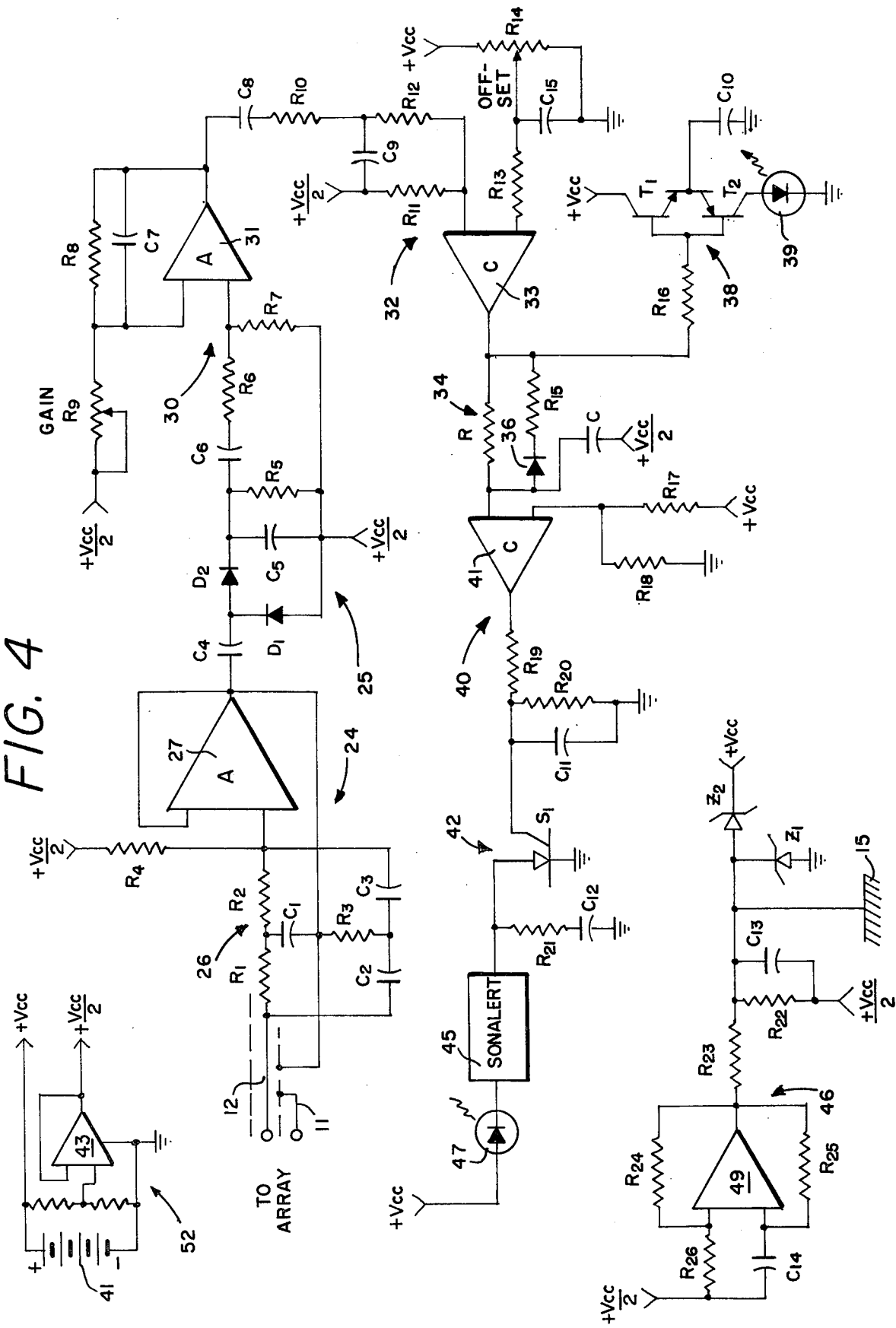
FIG. 4 is a schematic diagram of a preferred embodiment of the electronic circuits shown in FIG. 2.

Referring now to FIG. 4, I show a preferred schematic diagram of the apnea monitoring system of FIG. 2 which utilizes discrete components for explanatory purposes. A regulated power supply 52 is used having a nickel cadmium battery 41 and voltage regulator circuit 43 which produces two output voltages $+V_{cc}$ and $+\frac{1}{2}V_{cc}$. Although not shown, I prefer to provide a standard battery charging circuit for battery 41 which is normally connected to the household power circuit. Thus, the charger maintains battery 41 at full charge at all times with battery 41 serving as an emergency power supply during occasional power outages. Preamp 24 may utilize a type TLO64 operational amplifier. A 60 Hz notch filter 26 is formed by resistors R1, R2 and R3 and capacitor C1, C2 and C3 in a bridged-T connection.

Rectifier 25 is formed from a voltage doubler circuit using diodes D1, D2 and capacitor C4 and C5. The output of rectifier circuit 25 is capacitively coupled to amplifier 30 which may use a type TLO64 amplifier 31. Variable resistor R9 is used to vary the gain of amplifier 30.

Comparator 32 may use a type TLO64 integrated circuit connected as a comparator. Its threshold is set by potentiometer R14. As mentioned above, potentiometer R14 is set so that the output from comparator 32 is HIGH when the circuit is in its quiescent state. RC circuit 34 may utilize a 0.47 uf capacitor and a 10 megohm resistor producing a time constant of about five seconds. When the output of the comparator is HIGH, capacitor C will charge through resistor R. However, when the output of comparator 32 is LOW, the low impedance discharge path via diode 36 will cause transistor T2 to conduct discharging capacitor C very quickly. During the time that comparator 32 has a HIGH output, transistor T2 will conduct; charging capacitor C10 which may be a 47 uf unit. During the LOW condition, transistor T1 is cut off and capacitor C10 discharges through transistor T2 illuminating LED 39. Thus, capacitor C is quickly discharged for the next charge cycle and each movement is indicated by a flash of LED 39.

Comparator 40 may use a type TLO64 op amp and has a threshold set by the values of resistors R17 and R18. As described with reference to line E of FIG. 3, the absence of inputs to comparator 32 will cause the voltage across capacitor C to increase to the point that the threshold of comparator 40 is reached. This produces a high at the output of comparator 40, triggering SCR 42. SCR 42 may be a General Electric type C103. Since SCR 42 has its anode voltage supplied from the dc voltage $+V_{cc}$, it will conduct continuously after triggering and will energize a Sonalert sound alarm 45 and LED visual alarm 47. The alarm elements may be, of course, located in another room from the infant being monitored or may be a local alarm as desired.

50 kHz oscillator 46 may be implemented by a type TLO64 integrated circuit connected to produce square waves at about 50 Hz. Zeners $Z_1$ and $Z_2$ serve to place a short circuit on supply voltage $V_{cc}$ in the event that a line connected battery charger developed a leakage between the power line and the monitor circuit. Thus, a fuse in the charger circuit or low current diodes would blow, isolating the circuit from the power line.

It may be noted that all of the amplifiers used in my preferred implementation are BI-FET op amps available in a quad configuration as type TLO64. Therefore, only two such integrated circuits are required.

Although other values of components are satisfactory for the circuit of FIG. 4, the following is a tabulation of preferred values:

|  | Ohms |  | Ohms |  |  |
| --- | --- | --- | --- | --- | --- |
| $R_1$ | 10M | $R_{18}$ | 10M | $C_7$ | 0.01 uf |
| $R_2$ | 10M | $R_{19}$ | 10k | $C_8$ | 0.47 uf |
| $R_3$ | 5M | $R_{20}$ | 3.9k | $C_9$ | 0.001 uf |
| $R_4$ | 10M | $R_{21}$ | 10M | $C_{10}$ | 47 pf |
| $R_5$ | 220k | $R_{22}$ | 10k | $C_{11}$ | 0.01 uf |
| $R_6$ | 220k | $R_{23}$ | 1k | $C_{12}$ | 0.01 uf |
| $R_7$ | 10M | $R_{24}$ | 220k | $C_{13}$ | 0.01 uf |
| $R_8$ | 10M | $R_{25}$ | 220k | $C_{14}$ | 270 pf |
| $R_9$ | 60k | $R_{26}$ | 220k |  |  |
| $R_{10}$ | 100k | $R_{27}$ | 100k | $T_1$ | 2N2906 |
|  |  | $R_{28}$ | 100K |  |  |
| $R_{11}$ | 10M | C | 0.47 uf | $T_2$ | 2N3904 |
| $R_{12}$ | 10k | $C_1$ | 540 pf |  |  |
| $R_{13}$ | 10M | $C_2$ | 270 pf | $Z_1$ | 9.1v. |
| $R_{14}$ | 1M | $C_3$ | 270 pf | $Z_2$ | 9.1v. |
| $R_{15}$ | 10k | $C_4$ | 0.1 uf |  |  |
| $R_{16}$ | 10k | $C_5$ | 0.1 uf |  |  |
| $R_{17}$ | 1M | $C_6$ | 0.02 uf |  |  |

For purposes of explanation, my detection circuits have been described using discrete components and two integrated circuit chips. However, it will be obvious to those of skill in the art that the major portions of the circuits can be implemented by large scale integration. Therefore, the cost of the circuit in very large quantities can be greatly reduced. Other types of circuits may also be substituted for those shown in the preferred embodiment without departing from the spirit and scope of my invention.

I claim:

1. A device for monitoring an apnea episode or the like of a person wherein the dielectric constant of said person varies with breathing comprising:
   a pad formed from an electrically conductive material having two sides, a first side thereof for positioning adjacent to a person to be monitored;
   a single ended voltage follower preamplifier having an input connected to said pad, said preamplifier having a circuit ground floating with respect to earth ground;
   a guard shield disposed on the second side of said pad and insulated therefrom, said guard shield connected to the output of said preamplifier;

a carrier oscillator having a common circuit ground with said preamplifier and having a carrier output signal connected to said earth ground whereby said oscillator pumps said preamplifier at the frequency of oscillation whereby breathing movements of said person produce changes in dielectric constant between said grid and said earth ground thereby modulating said carrier signal;

demodulator means connected to said preamplifier output for extracting a time varying signal from such modulated carrier signal proportional to such breathing movements;

detection means connected to said demodulator means for determining the presence or absence of said time varying signal;

a low frequency amplifier capacitively coupled to said demodulator means;

first comparator means having an adjustable threshold for producing a HIGH output in the absence of a demodulated signal and a LOW output in the presence of a demodulated signal;

integrator means connected to the output of said first comparator means for producing a voltage proportional to the time of absence of a demodulated signal;

discharge means for rapidly discharging said integrator in the presence of a demodulated signal;

indicating means connected to the output of said integrator for indicating the presence of a demodulated signal and for indicating the absence of a demodulated signal for a preselected period of time.

2. The device as defined in claim 1 in which said device for indicating the absence of a demodulated signal comprises:

a second comparator means having a threshold so as to produce a HIGH output therefrom when the voltage output of said integrator means rises to a preselected value indicative of said preselected time; and alarm circuit means connected to the output of said second comparator means for producing an alarm when said output is HIGH.

3. The device as defined in claim 1 in which said means for indicating the presence of a demodulated signal comprises:

current sensing means for producing a voltage when said integrator means is discharged; and switch means connected to and responsive to said current sensing means for producing an output signal when such discharge current is sensed.

4. The device as defined in claim 1 which includes a notch filter connected between said pad and said voltage follower preamplifier for rejecting power line interference.

5. A system for detecting motion of a body comprising:

(a) an earth ground;

(b) a capacitance electrode having a first and second surface and floating with respect to said earth ground, said body in motion disposed adjacent said first surface of said capacitance electrode to tereby produce a time varying dielectric between said electrode and said earth ground;

(c) a voltage follower amplifier having an input circuit connected to said electrode, said amplifier having a circuit ground floating with respect to said earth ground;

(d) shielding means disposed adjacent said second surface of said electrode for minimizing variation in capacitance between said electrode and earth ground from other than said body;

(e) a carrier frequency oscillator having a circuit ground common with said voltage follower amplifier and a carrier output connected to said earth ground whereby said oscillator pumps said electrode with respect to said earth ground, said time varying dielectric varying the capacity between said electrode and said earth ground thereby modulating said carrier output at the rate of time variation of said dielectric producing a modulated carrier signal at the output of said voltage amplifier; and (f) detection means connected to said voltage follower amplifier output for detecting the presence and absence of said modulation of said carrier.

6. The system as defined in claim 5 in which said shielding means comprises a guard shield electrode connected to the output of said voltage follower and disposed adjacent to said capacitance electrode such that the capacitance electrode is between said body and said guard shield electrode.

7. A method of monitoring the motion of a body comprising the steps of:

disposing a grid electrode adjacent the body to be monitored;

disposing shielding means between the grid electrode and an earth ground;

pumping the said grid electrode with respect to the earth ground with an electrical carrier frequency with respect to said electrode by means of an oscillator having a floating circuit ground;

producing a modulated carrier voltage between said electrode and said circuit ground when motion of the body occurs;

amplifying the modulated carrier voltage by an amplifier having a circuit ground common with said oscillator and an output connected to the shielding means;

demodulating the modulated carrier voltage at the output of the amplifier to produce a modulation envelope when motion of the body occurs;

providing a first indication when a modulation envelope is produced; and providing a second indication when the modulation envelope is absent for a preselected time period.

* * * * *